(12) United States Patent
D'Amelio et al.

(10) Patent No.: US 6,234,205 B1
(45) Date of Patent: *May 22, 2001

(54) SURGICAL PROBE ADAPTED FOR SMOKE EVACUATION

(75) Inventors: Frank D. D'Amelio, Los Olivos, CA (US); Dennis Reisdorf, Racine, WI (US); John Johnston, Washington, NJ (US)

(73) Assignee: Cabot Technology Corporation, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/889,645

(22) Filed: Jul. 8, 1997

(51) Int. Cl.[7] ....................................................... F16K 11/02
(52) U.S. Cl. ................................ 137/625.17; 137/625.28; 604/246
(58) Field of Search ........................ 137/625.17, 625.28, 137/636.4; 251/117; 604/246, 248, 249

(56) References Cited

U.S. PATENT DOCUMENTS

| 4,653,535 | * | 3/1987 | Bergmann | 137/625.17 |
|---|---|---|---|---|
| 5,188,591 | | 2/1993 | Dorsey, III . | |
| 5,303,735 | | 4/1994 | Cerola et al. . | |
| 5,348,555 | | 9/1994 | Zinnanti . | |
| 5,391,145 | | 2/1995 | Dorsey, III . | |
| 5,449,145 | | 9/1995 | Wortrich . | |
| 5,449,357 | | 9/1995 | Zinnanti . | |
| 5,522,796 | | 6/1996 | Dorsey, III . | |
| 5,526,845 | * | 6/1996 | Manos | 137/625.17 |

* cited by examiner

Primary Examiner—John Fox
(74) Attorney, Agent, or Firm—Austin R. Miller (57) ABSTRACT

A valved device is provided for controlling flow into or out from a surgical patient. It includes a body defining a flow passageway and a valve connected to the body in flow communication with the body's passageway. The valve includes a barrel and a piston extending into the barrel. Means is provided for displacing the piston within the barrel along the barrel's axis to open a flow path that is preferably adapted for liquid suction. Means is also provided for rotating the piston within the barrel around the barrel's axis to open a flow path that is preferably adapted for smoke or gas evacuation.

21 Claims, 9 Drawing Sheets

SURGICAL PROBE ADAPTED FOR SMOKE EVACUATION

BACKGROUND OF THE INVENTION

This invention relates to a probe for use during surgical procedures. In particular, this invention relates to a probe for fluid flow into or out from a surgical patient, wherein the probe provides a flow path adapted for liquid flow and a flow path adapted for gas flow.

FIELD OF THE INVENTION

The rapid increase in the use of endoscopic surgical techniques has created a rising demand for new surgical devices. Unlike traditional surgical techniques during which a surgical site is exposed by relatively large incisions, endoscopic techniques permit access to the site through one or more small openings. The surgical site, which remains substantially closed, is inflated by insufflation or pneumoperitoneum or is mechanically distended in order to allow access for the surgeon to perform a procedure.

During endoscopic procedures such as laparoscopic surgery, irrigation fluid is often delivered to the surgical site to aid visualization and wash out the site. Irrigation fluid must be subsequently removed to avoid over-accumulation. Also, there is sometimes a need to use laser or electrosurgical devices to vaporize, cut, or cauterize tissue within the operative site. These techniques tend to generate smoke or other gases that may become trapped within the confines of the distended surgical site. If permitted to accumulate, such smoke can obscure the surgeon's view through a scope. Also, the odor of such smoke may cause discomfort to exposed individuals.

Various devices are currently available for delivering fluid into, and for suction of fluid from, a surgical site. For example, "suction-irrigation probes" are offered under the trademarks CORSON and SURGIFLEX by Circon Cabot of Racine, Wis. It has been proposed that controlled opening of the suction valve of such probes can remove cautery smoke from a surgical site in order to maintain or regain visualization. For example, U.S. Pat. Nos. 5,188,591 and 5,391,145, both to James H. Dorsey, III, explain that the degree to which a suction valve's piston is reciprocated within the valve's cylinder modulates the flow through the valve. The farther the piston is depressed within the valve chamber, the greater the flow of fluid. Such valve control can be tricky, however. Inadequate suction tends to permit smoke accumulation over time until the insufflated site is clouded throughout. Such a condition can require removal and replacement of insufflation gas. On the other hand, too much gas suction can deflate the insufflated site when it exceeds the insufflation rate. When re-insufflation of an operative site is required, the surgical procedure can be significantly prolonged, which of course is undesirable from the perspective of the surgeon and the patient.

Attempts have been made to adapt suction and irrigation probes for smoke evacuation. One design concept is proposed in U.S. Pat. Nos. 5,348,555 and 5,449,357, both to William J. Zinnanti, which describe a suction valve provided with an adjustable stop in order to control its opening and to control the application of vacuum at the open end of a lumen. A nut limits the down-stroke of the valve's piston to limit the suction volume. It is intended to permit a surgeon to maintain suction without losing the space created by the insufflation or pneumoperitoneum.

Another design concept is proposed in U.S. Pat. No. 5,303,735 to Joseph J. Cerola and U.S. Pat. No. 5,522,796 to James H. Dorsey, III, which describe a valve having a separate actuator intended to enable limited depression of the piston to a location between a fully closed position and an intermediate position between a fully open position and the fully closed position. Cerola describes a rotatable thumb wheel that can be used by a surgeon to rotate a cam which rides against a cam-following element on the valve's piston. Cam rotation is intended to depress the piston while a vertical guidearm prevents piston rotation. Dorsey describes a valve piston that is incrementally depressed a precise distance to open the valve and maintain the valve at such a setting. A knob on the side of the Dorsey valve is rotated and a cam depresses a keyed piston.

Despite these attempts to adapt a suction-irrigation probe for smoke evacuation, there remains a need for an improved probe that is adapted for both suction of liquids and aspiration of gases, as needed, and that is simple and easy to operate.

OBJECTS OF THE INVENTION

It is an object of this invention to provide a probe adapted for suction or irrigation of liquid or gaseous fluid during a surgical procedure.

It is another object of this invention to provide a probe that is simple and easy to use for alternative liquid suction and gas evacuation.

Other objects of this invention will be clear in view of the following description.

SUMMARY OF THE INVENTION

A valved device is provided for controlling flow into or out from a surgical patient. The valved device includes a body portion defining a flow passageway through which fluid flows toward or away from the patient. A valve is connected to the body so that fluid flow is permitted between the body's flow passageway and the valve's interior. The valve includes a barrel and a piston that extends into the barrel.

A means is provided for displacing the piston within the barrel in a general direction along the barrel's axis. Such displacement permits fluid flow into or out from the patient. The flow path thus opened is preferably suitable for liquid suction. Also provided is a means for rotating the piston within the barrel around the barrel's axis to permit flow. This flow path is preferably separate from the other flow path and is preferably adapted for smoke or gas evacuation from the surgical site.

DETAILED DESCRIPTION OF THE INVENTION

It will be appreciated that this invention is not limited to the specific embodiments selected for illustration in the drawings and described herein. It will also be appreciated that the drawings are merely illustrative and are not necessarily to scale and that the invention is defined separately in the appended claims.

Figure 1:
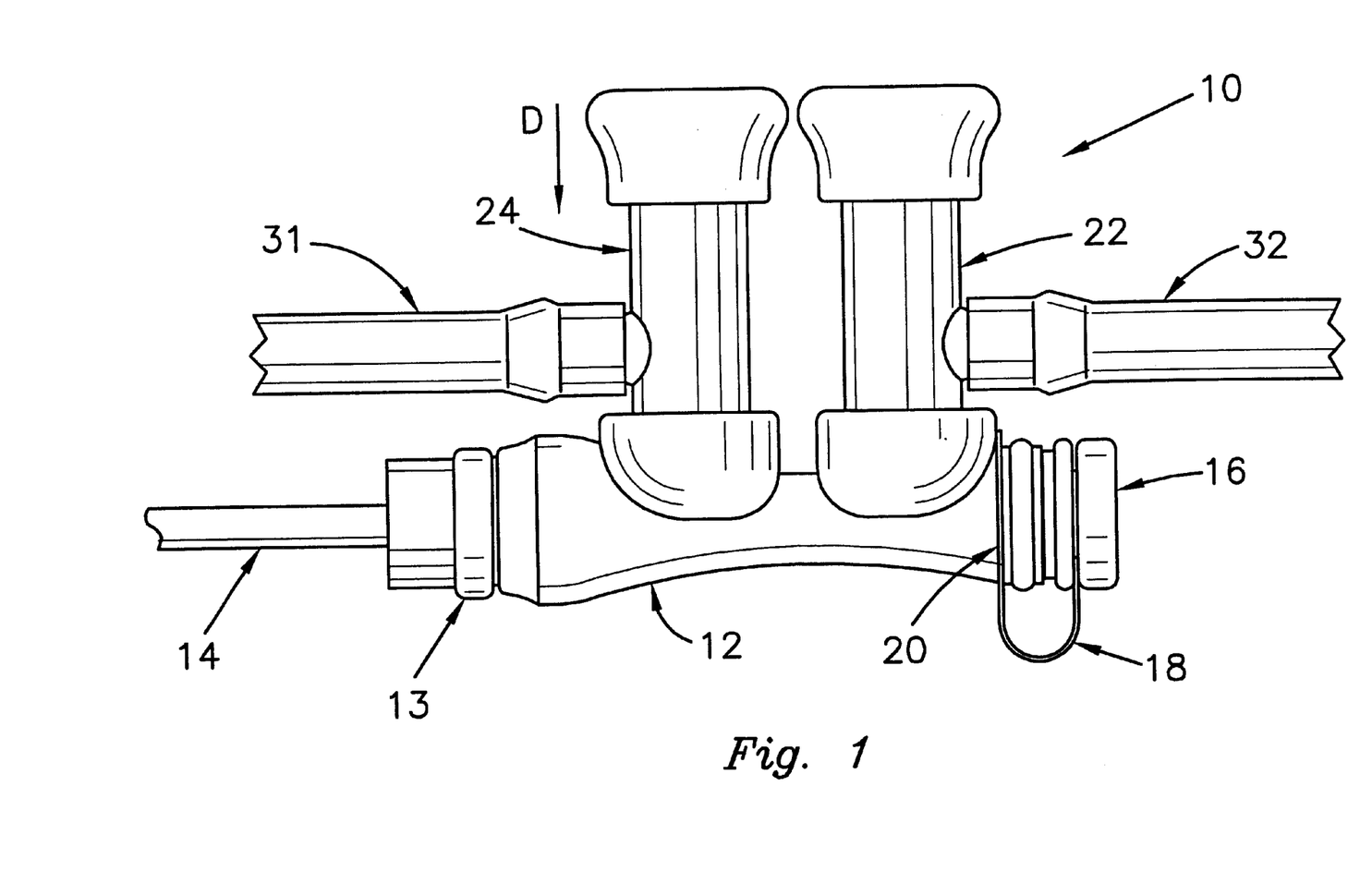
FIG. 1 shows a side view of an embodiment of a suction-irrigation probe according to this invention.
Figure 2:
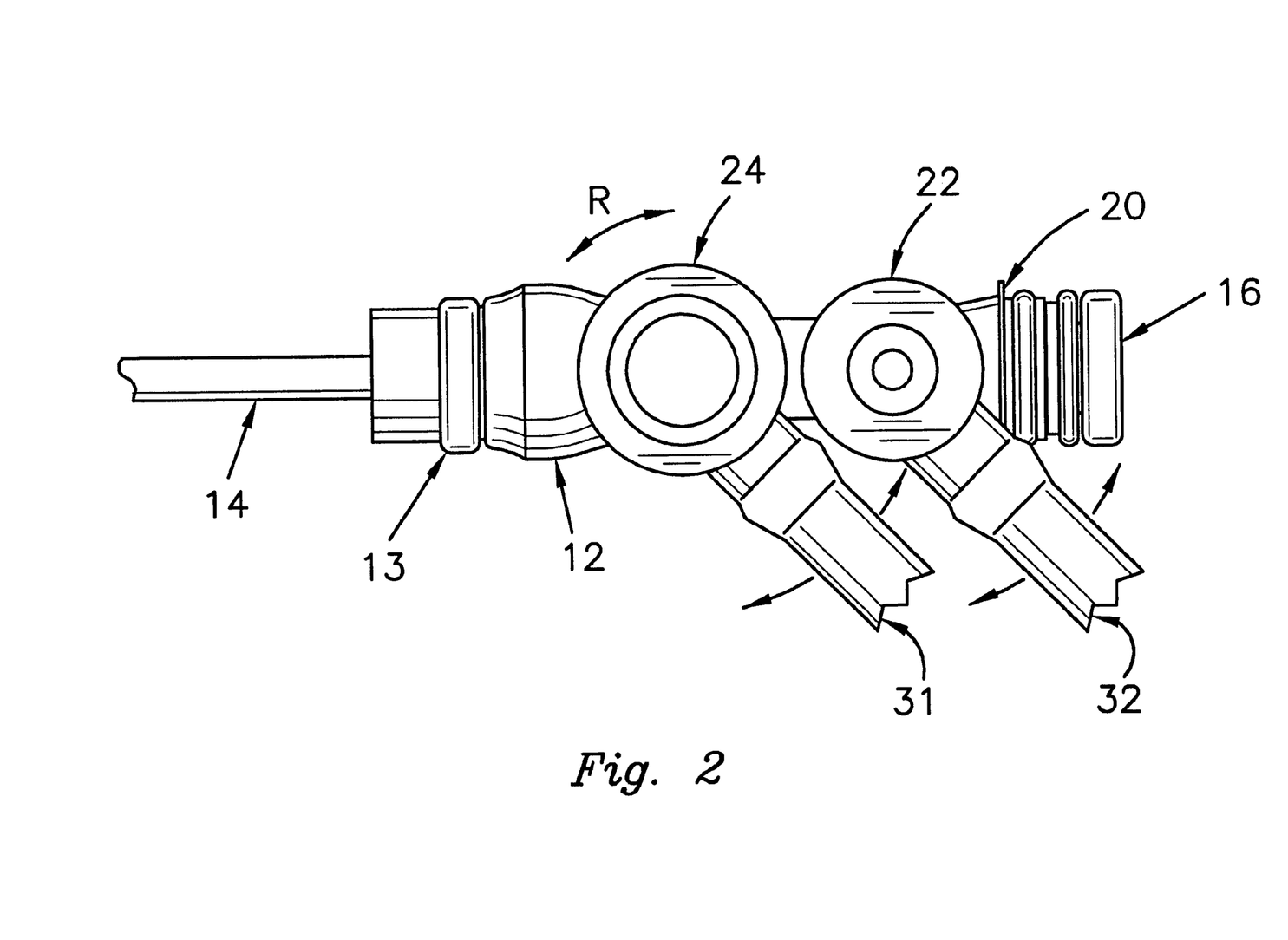
FIG. 2 shows a top view of the suction-irrigation probe shown in FIG. 1.
Figure 3:
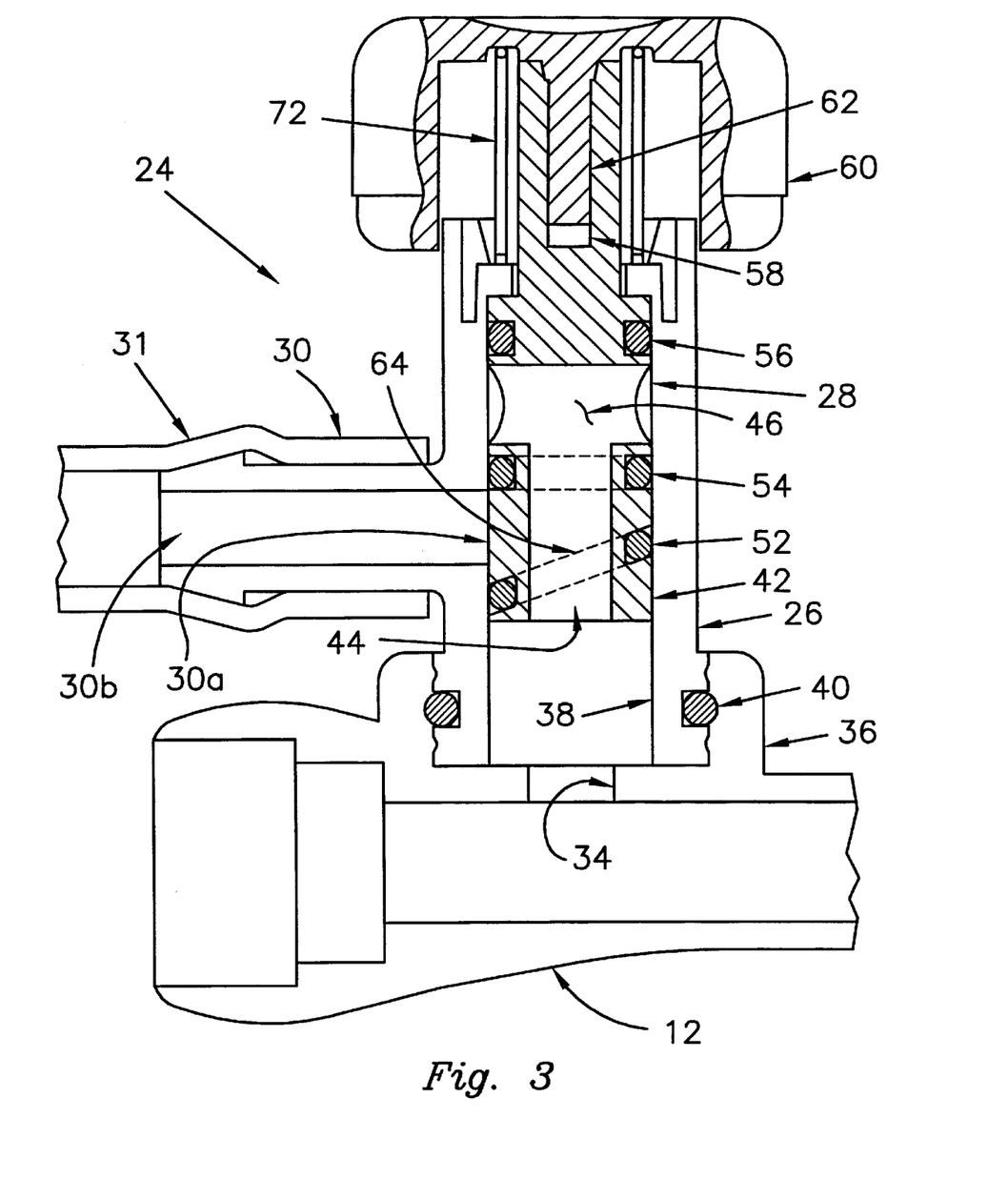
FIG. 3 shows a cross-sectional side view of a portion of the suction-irrigation probe shown in FIG. 1.

FIGS. 1–3 illustrate an embodiment of a probe according to this invention, generally indicated by the numeral "10". Although the embodiment of probe 10 selected for illustration is adapted for suction and irrigation of an operative site by removing and introducing fluid from and to the site, respectively, this invention applies equally to probes that are solely used for suction or for irrigation as well as any other types of probes that could benefit from features of the invention. Unless the contrary is indicated, the term "fluid" refers to a liquid and/or gas. Also, this invention applies to probes that are intended for disposable use as well as those intended for sterilization and re-use. While probe 10 is described in the context of laparoscopic surgical procedures and related procedures, other applications or procedures are of course contemplated.

Referring to FIG. 1, probe 10 includes a probe body portion 12 that is sized and shaped to be held within the hand of a surgeon during a medical procedure. Although not shown, body 12 optionally includes a palm rest. Probe body 12 (and other main components of probe 10) is preferably molded from a polymeric or plastic material such as clear, translucent or opaque ABS or acrylic, for example. Probe 10 also includes a tubular probe shaft 14 extending from an end of probe body 12 and connected to body 12 by an adapter or connector 13. Probe shaft 14 is adapted for insertion into a patient and into an operative site in the conventional manner. An end cap 16 is provided at the opposite end of probe body 12 from probe shaft 14. End cap 16 is sized and shaped to prevent the flow of liquid or gaseous fluid from the probe body 12. End cap 16 is attached by means of a strap 18 that is connected to an attachment ring 20 positioned around the end of probe body 12. End cap 16 is removable and replaceable so that surgical instruments, such as electrocautery probes for example, can be inserted through probe body 12, through probe shaft 14, and into the operative site.

Probe 10 also includes an irrigation valve 22 and a suction valve 24, both of which extend upwardly from the top surface of probe body 12 in this embodiment. The irrigation valve 22 is adapted to control the delivery of liquid or gaseous fluid, such as irrigation liquid for example, into the operative site. Such fluid is delivered to irrigation valve 22 through a flexible hose 32. The suction valve 24 is adapted to control the suction or aspiration or evacuation of liquid or gaseous fluid, such as irrigation fluid, blood, and smoke for example, from the operative site. Such fluid is removed from suction valve 24 through a flexible hose 31. Such a valve system is frequently referred to as a so-called "trumpet valve". The operation of valves 22 and 24 to control suction and irrigation will be described later.

Referring now to FIG. 2, a top view of probe 10 illustrates an optional feature of this invention. As indicated by the arrows adjacent to hoses 31 and 32, the irrigation valve 22 and suction valve 24 are preferably connected to probe body 12 for rotation about their respective axes so that their barbed fluid connections can be rotated into a variety of positions with respect to the axes of probe body 12 and probe shaft 14. In FIG. 2, both of the barbs are oriented in substantially the same direction but can be rotated in either direction, as needed or desired. This optional feature permits the user of probe 10 to rotate valves 22 and 24 and their respective fluid hoses 31 and 32 either prior to a medical procedure, during a medical procedure, or even "on the fly" during use of probe 10 for suction or irrigation of an operative site. Such "on the fly" adjustment can preferably be performed while suction or irrigation is underway and while the probe shaft 14 remains in the patient. This preferred feature permits the user or users to adapt probe 10 at any time to be comfortably held in the right hand, the left hand, for alternative movement between the right and left hands, or merely for adjustment of the relative positions of the suction and irrigation hoses so that they do not interfere with surgical activities. Further details of this preferred feature are provided in co-pending U.S. patent application Ser. No. 08/889,654, filed Jul. 8, 1997, which is incorporated herein by reference and assigned to the assignee hereof.

A preferred structure of suction valve 24 will be described with reference to FIG. 3. Details of irrigation valve 22 are not shown, but it will be appreciated that the structure of both valves may be the same or substantially the same. In the illustrated embodiment, suction valve 24 is adapted to remove fluid from a surgical site in the form of a liquid or a gas while the irrigation valve 22 is adapted to control the flow of irrigation liquid into the surgical site. As shown in FIG. 2, the tops of the valves preferably differ so that a surgeon can quickly differentiate between them.

Suction valve 24 includes a so-called "smoke evacuation" feature and is adapted to facilitate partial suction or "sipping" of an operative site. Such "sipping" is preferred for smoke or vapor evacuation which may be necessary when a cauterization procedure conducted in the operative site generates smoke that obstructs the surgeon's view, as described earlier.

As shown in FIG. 3, suction valve 24 includes a barbed tube 26 defining at least a portion of a substantially cylindrical and hollow valve barrel 28 as well as a barb 30 that extends radially outwardly from barrel 28 to form a valve port. Barb 30 of barbed tube 26 is adapted for engaging an end of a flexible hose 31 such as those commonly used for delivery or removal of liquid or gaseous fluids to or from a surgical site. Flexible hose 31 is connected to a known suction source (not shown).

Barbed tube 26 is connected to probe body 12 adjacent to a body opening 34 formed in probe body 12. Accordingly, when suction valve 24 is in an open position (not shown), a passageway is defined for the flow of liquid or gaseous fluids through probe shaft 14, through probe body 12, upward through opening 34, through barrel 28, and out through barb 30 and hose 31. Barb 30 has a passageway 30(b) and an open end 30(a) through which fluid may flow.

A preferred manner in which barbed tube 26 can be mounted to probe body 12 is depicted in FIG. 3 and is described in further detail in co-pending U.S. patent application Ser. No. 08/889,654, filed Jul. 8, 1997 and assigned to the assignee hereof. Probe body 12 includes a boss 36 which defines body opening 34 which accommodates a mounting portion 38 of barbed tube 26. Mounting portion 38 captures an O-ring 40 to create a fluid-tight seal between probe body 12 and barbed tube 26 to prevent leakage into or out from the probe body between those components. Mounting portion 38 is adapted to permit rotation of barbed tube 26 about the vertical axis of barrel 28 (in this embodiment) while maintaining a fluid-tight seal between the components. Further, this connection is adapted to withstand high pull-out forces so that barbed tube 26 cannot be easily separated from probe body 12, even during the most rigorous use of probe 10.

Still referring to FIG. 3, suction valve 24 also includes a piston 42 that is mounted for reciprocal longitudinal movement within barrel 28 of barbed tube 26 along a piston axis. Piston 42 is provided with a piston bore 44 along the piston's axis to permit the flow of fluid therethrough. Piston 42 is also provided with a transverse circular through-hole 46 that is in fluid flow communication with, and substantially perpendicular to, piston bore 44.

Seals are provided between an outer surface of piston 42 and the interior surface of barrel 28 by means of three O-rings. A lower O-ring 52 is provided in a groove closest to the bottom edge of piston 42. A middle O-ring 54 is provided in a groove positioned just below through-hole 46. An upper O-ring 56 is provided in a groove positioned above through-hole 46. FIG. 3 illustrates suction valve 24 in a closed valve position wherein piston 42 and O-rings 52, 54 and 56 cooperate to prevent fluid flow between the interiors of barrel 28 and barb 30. O-ring 54 prevents fluid flow into barb 30 from through-hole 46 and piston bore 44. O-ring 52 prevents fluid flow into barb 30 from between an outer surface of piston 42 and an interior surface of barrel 28. O-ring 56 prevents fluid flow into barb 30 from an open upper end of barbed tube 26. Although piston 42 and seals 52, 54 and 56 are illustrated as separate components in the embodiment shown in FIG. 3, piston 42 and the seals can be integrated into a single piston component. Accordingly, the term "piston" identifies a component adapted for assembly with one or more seals as well as a component that already includes one or more seals.

Piston 42 is provided with a shoulder above O-ring 56 for abutment against a stop formed near the top of barbed tube 26 for the purpose of preventing upward movement of piston 42 beyond the position shown in FIG. 3. In the top of piston 42 is formed a blind hole 58. Suction valve 24 also includes a finger rest 60 adapted for contact by the surgeon's finger during use of probe 10. Finger rest 60 includes a downwardly extending stud 62 which is adapted to be engaged within the blind hole 58 formed in the top of piston 42, preferably by bonding or ultrasonic welding, for example. Still referring to FIG. 3, a compression spring 72 is provided to bias the finger rest 60 toward its uppermost position as shown, wherein the shoulder of piston 42 contacts the stop at the top of barrel 28. Compression spring 72 is mounted between a lower surface of finger rest 60 and an upper surface of barbed tube 26 so that finger rest 60 and piston 42 are returned to the position shown in FIG. 3, when released.

FIG. 3 illustrates one possible embodiment of an important feature of this invention. It will be understood that depression of piston 42 downwardly along the axis of barrel 28 (with or without rotation of piston 42 with respect to the axis of barrel 28) will result in the opening of a flow path that extends from barb 30, through through-hole 46, downwardly through piston bore 44, through body opening 34 and into probe body 12. Full or partial alignment of through-hole 46 in piston 42 with barb 30 opens this flow path through the suction valve. This path can be considered a "primary" flow path because it can provide for maximum flow through the valve. For example, in this embodiment, through-hole 46 is fully aligned with barb 30 when finger rest 60 is fully depressed and a bottom surface of finger rest 60 stops against a top surface of barbed tube 26 or some other stop mechanism is provided. This primary flow path is preferably of sufficient size to accommodate tissue or other matter that is likely to be extracted from an operative site, together with fluid, during use of suction valve 24. Partial depression of piston can be conducted to provide for partial flow through the primary flow path, as desired.

Lower O-ring 52, or any equivalent seal of elastomeric or other material, is provided at an angle to the plane that is perpendicular to the axis of barrel 28. For example, the angle of an O-ring 52 with respect to a horizontal plane as shown in FIG. 3 is most preferably about 20°, although smaller and larger angles are contemplated as well. O-ring 52 is positioned at an angle by forming an angled O-ring groove 64 in the surface of piston 42 so that an appropriately-sized O-ring can be placed within the groove in order to provide a seal to prevent flow between an outer surface of piston 42 and an inner surface of barrel 28.

Finger rest 60 and piston 42 are mounted for rotation with respect to barrel 28 as indicated generally by the arrow "R" in FIG. 2. Although not shown, finger rest 60, barbed tube 26 and piston 42 can be easily adapted to limit the degree of rotation of piston 42 with respect to barrel 28. For example, one or more longitudinally extending ribs can be positioned on the piston for cooperation with one or more channels formed in the opening in the top of the barrel so that the edges of the channels limit the rotation of the piston. Also, detents or other means are optionally provided between finger rest 60, piston 42 and barbed tube 26 to indicate to the user of the device that incremental degrees of rotation are occurring as the piston rotates and to hold piston 42 with respect to barbed tube 26 at a desired position selected by the surgeon, although such means are not required.

It will be understood by one of skill in the art that rotation of piston 42 with respect to barbed tube 26 causes a portion of O-ring 52 (the highest portion in this embodiment) to traverse a portion of the passageway defined by barb 30. In other words, as lower O-ring 52 is rotated together with piston 42 while piston 42 is preferably maintained in the vertical position shown in FIG. 3, a portion of O-ring 52 that is positioned at a vertical height above that of the lower-most portion of the wall of barb 30 will become at least partially aligned with the barb 30, and that portion of O-ring 52 traverses a portion of barb 30. Upon such rotation, a controlled path for flow between barb 30 and barrel 28 is formed, wherein the path extends from barb 30, downward around the outer surface of piston 42, and into barrel 28. This flow path can be considered a "secondary" flow path. It is preferably substantially separate from the primary flow path described above, which extends through the body of the piston. This flow path can be considered secondary because it permits a flow path that is adapted for smoke or gas evacuation. Such a secondary path is preferably smaller in cross-sectional area than the primary path. Partial rotation of piston 42 permits various degrees of flow while rotation by about 180° (for the embodiment illustrated in FIG. 3) results in a maximum flow through the secondary path. Smaller or larger angles than 180° can be used for maximum smoke evacuation flow as well. This secondary flow path is preferably opened by rotation of the piston 42 without any movement of the piston along the axis of barrel 28. Referring to FIG. 3, for example, rotation of piston 42 opens the secondary flow path without depression of piston 42 in the direction "D" (FIG. 1).

Although operation of suction valve 24 will be described in further detail later, it will be appreciated that depression of finger rest 60 and piston 42 with respect to barbed tube 26 in the direction identified as "D" in FIG. 1 will move piston 42 anywhere from the closed valve position shown in FIG. 3 to a fully open valve position when finger rest 60 is fully depressed to the end of its travel, thereby opening a primary flow path. This can be accomplished with or without rotation of the piston. Also, rotation of finger rest 60 and piston 42 with respect to barbed tube 26 in the direction generally indicated by "R" in FIG. 2, without depression of piston 42 and while piston 42 remains in its uppermost position shown in FIG. 3, will open a secondary flow path as a portion of lower O-ring 52 traverses barb 30. If desired, piston 42 can be maintained in a rotated position to open the secondary path and piston 42 can subsequently be depressed to open the primary path as well, and later released to close the primary path as the secondary path remains open. In other words, depressing piston 42 while in a smoke evacuation position will allow full aspiration. When released, piston 42 returns to the smoke evacuation position which is desirable to the surgeon. If desired, cam-type slots or other mechanisms are optionally provided to return piston 42 from the smoke evacuation position to the closed position.

Figure 12:
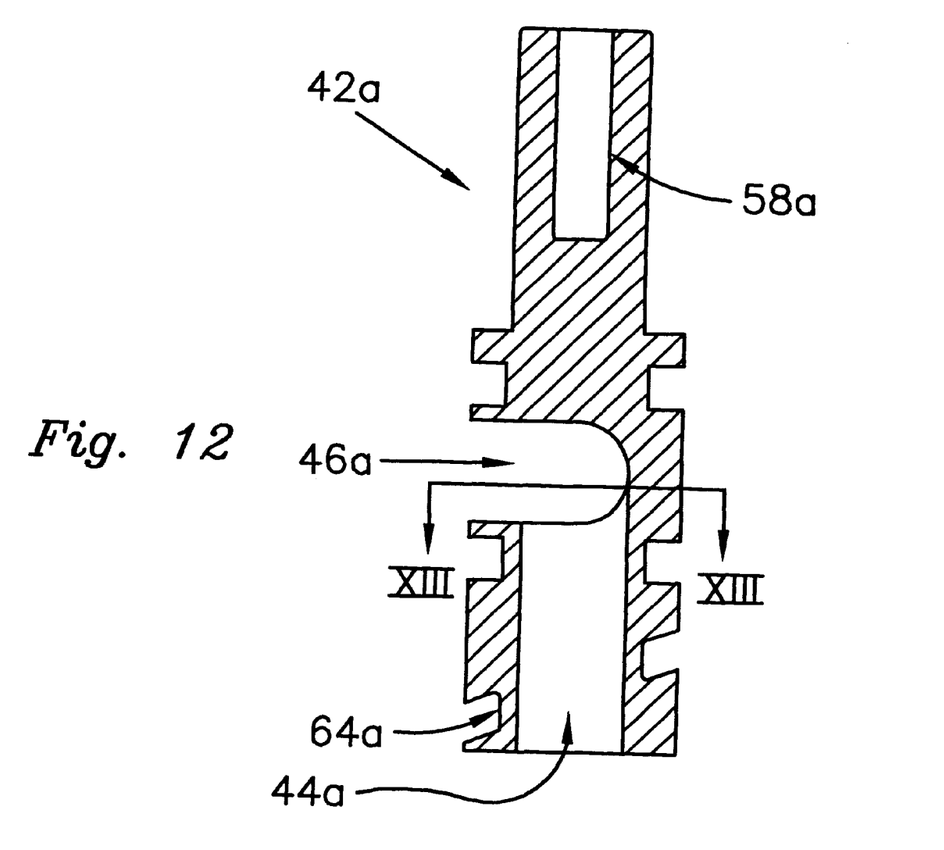
FIGS. 12 and 13 show cross-sectional views of a component adapted for use in the probe shown in FIG. 3.
Figure 13:
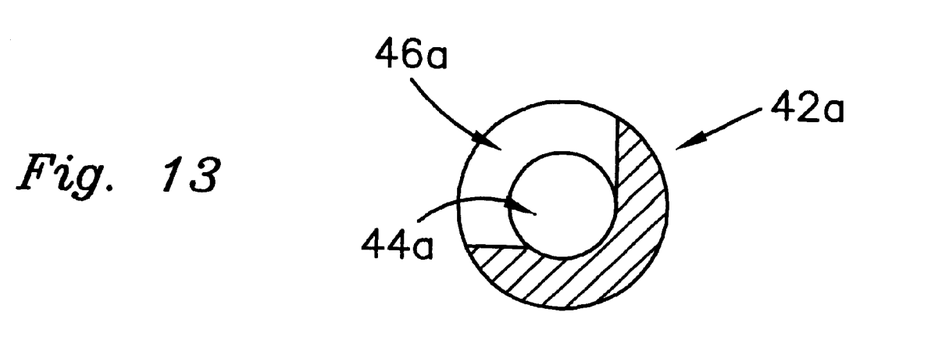

FIGS. 12 and 13 illustrate a preferred piston embodiment "42a" that is adapted for use in suction valve 24 illustrated in FIG. 3. Like piston 42, preferred piston 42a is intended for mounting for reciprocal longitudinal movement within barrel 28 of barbed tube 26 along a piston axis. Piston 42a is provided with a piston bore 44a, an angled O-ring groove 64a, and a blind hole 58a—each of these features having essentially the same structure and function as the corresponding features in piston 42. However, piston 42a differs from piston 42 in that it is provided a modified horizontal opening 46a that is in fluid flow communication with piston bore 44a. Referring specifically to FIG. 13, it will be appreciated that opening 46a extends radially about a portion of the circumference of piston 42a. Also, unlike through-hole 46, opening 46a does not extend all the way through piston 42a. Instead, it is closed on one end with the hole 46a being opened up into a transversely elongated slot.

The advantage of piston 42a is that it allows full aspiration through the suction valve 24 even when piston 42a is in a smoke evacuation position. In other words, opening 46a assures that rotation of piston 42a will not obstruct communication between piston bore 44a and the valve's barb when piston 42a is in a smoke evacuation position and piston 42a is depressed for full or partial aspiration. This features eliminates the need to rotate piston 42a out of the smoke evacuation position, and back to its original position, in order to accomplish full aspiration by depressing the piston.

Figure 4:
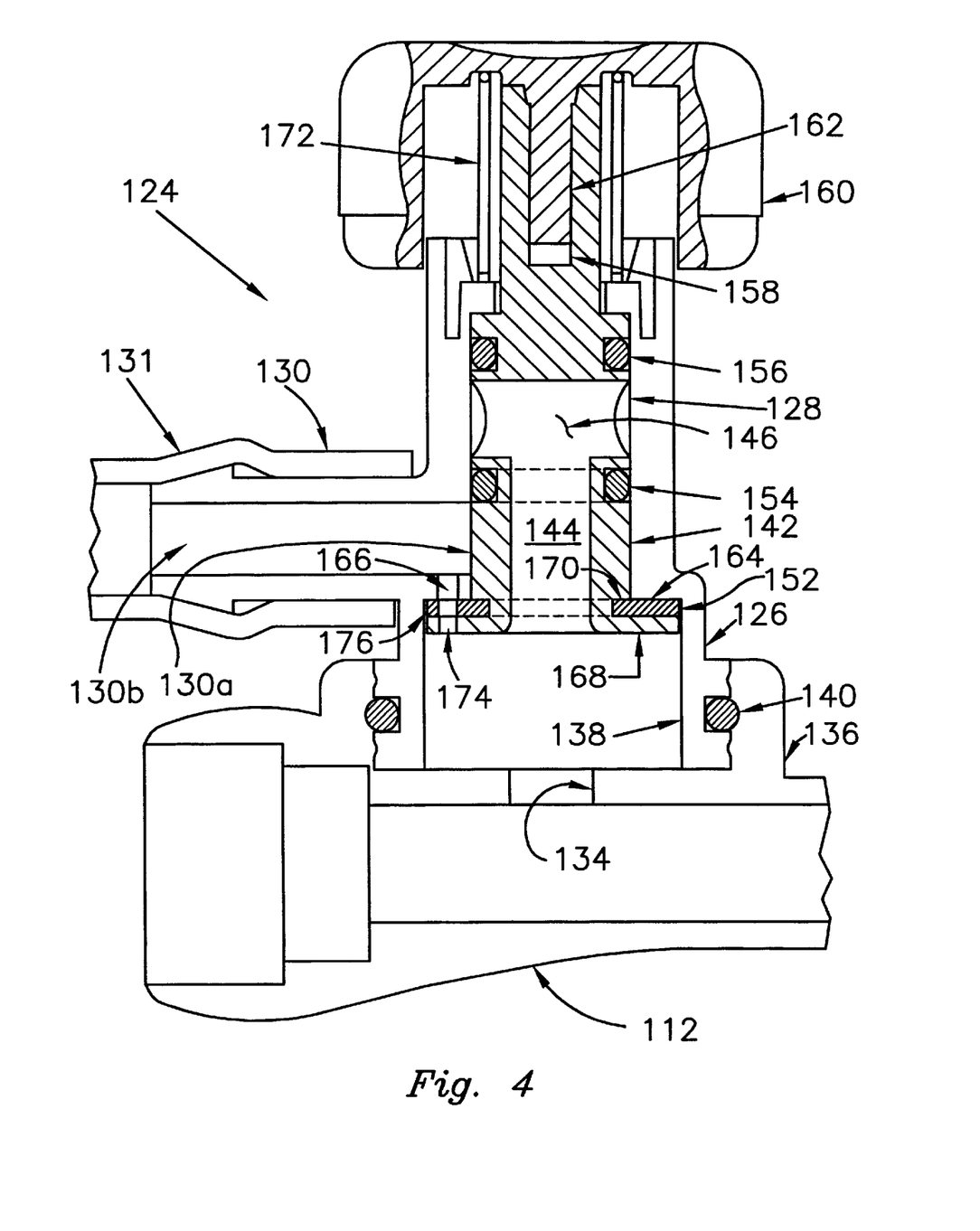
FIG. 4 shows a cross-sectional side view of a portion of another embodiment of a suction-irrigation probe according to this invention.

Referring now to FIG. 4, a cross-sectional side view of a portion of another embodiment of a probe according to this invention is illustrated, wherein this probe embodiment is generally designated by the numeral "100".

A suction valve 124 includes a barbed tube 126 having a hollow valve barrel 128 and a barb 130 that extends radially outwardly from the wall of barrel 128 to form a valve port. Barb 130 of barbed tube 126 is adapted for engaging an end of a flexible hose 131 that is connected to a suction source (not shown).

Barbed tube 126 is connected to a probe body 112 adjacent to a body opening 134 defined in a boss 136. When suction valve 124 is in an open position, a passageway is defined through the probe shaft (not shown), into probe body 112, upward through opening 134, through a portion of barrel 128, and out through barb 130 and hose 131. Opening 134 accommodates a mounting portion 138 of barrel 128 and an O-ring 140 creates a fluid-tight seal. Mounting portion 138 of barrel 128 is uniquely adapted to permit rotation of barbed tube 126 about the vertical axis of barrel 128 in the same manner as described earlier with reference to probe 10.

Suction valve 124 includes a piston 142 mounted for reciprocal longitudinal movement within barrel 128 along a piston axis. Piston 142 is provided with a piston bore 144 and a transverse circular through-hole 146. Through-hole 146 is optionally modified in the manner of opening 46a (FIGS. 12 and 13). Unlike piston 42, piston 142 is provided with an outwardly extending flange 168 adjacent to its bottom end. A slotted passageway 174 is formed through flange 168, and a channel 170 is provided adjacent to flange 168. Seals are provided between piston 142 and the interior surfaces of barrel 128 by means of three seal components, each of which are most preferably formed from an elastomeric material. A lower seal 152, preferably provided in the form of a flat washer-shaped disc, has a hole that is engaged in channel 170 of piston 142 so that a surface of seal 152 is positioned adjacent to the upper edge of flange 168. Seal 152 is provided with a slotted passageway 176 that is aligned with slotted passageway 174 in the flange 168 of piston 142. Seal 152 is preferably bonded to the upper edge of flange 168 to prevent inadvertent misalignment between passageways 174 and 176. Seal 152 is adapted to form a seal between piston 142 and a shoulder 164 formed in barbed tube 126 and barrel 128 just below the opening defined by barb 130. Shoulder 164 also defines a slotted passageway 166 that extends between an interior passageway of barb 130 and an interior region of barrel 128. Seal 152 is most preferably formed from silicone material such as 0.040" thick silicone sheet (50 shore A), although equivalent seals are contemplated.

As in probe 10, an O-ring 154 is provided in a groove just below through-hole 146, and an upper O-ring 156 is provided in a groove positioned above through-hole 146. These O-rings 154 and 156 form radial seals between piston 142 and an interior surface of barrel 128.

Piston 142 is provided with a shoulder above O-ring 156 for abutment against a stop formed near the top of barbed tube 126 to prevent upward movement of piston 142 beyond the position shown in FIG. 4. A finger rest 160 includes a downwardly extending stud 162 engaged within a blind hole 158 formed in the top of piston 142. A compression spring 172, provided to bias the finger rest 160 toward its uppermost position as shown, is mounted between a lower surface of finger rest 160 and an upper surface of barbed tube 126.

Figure 5:
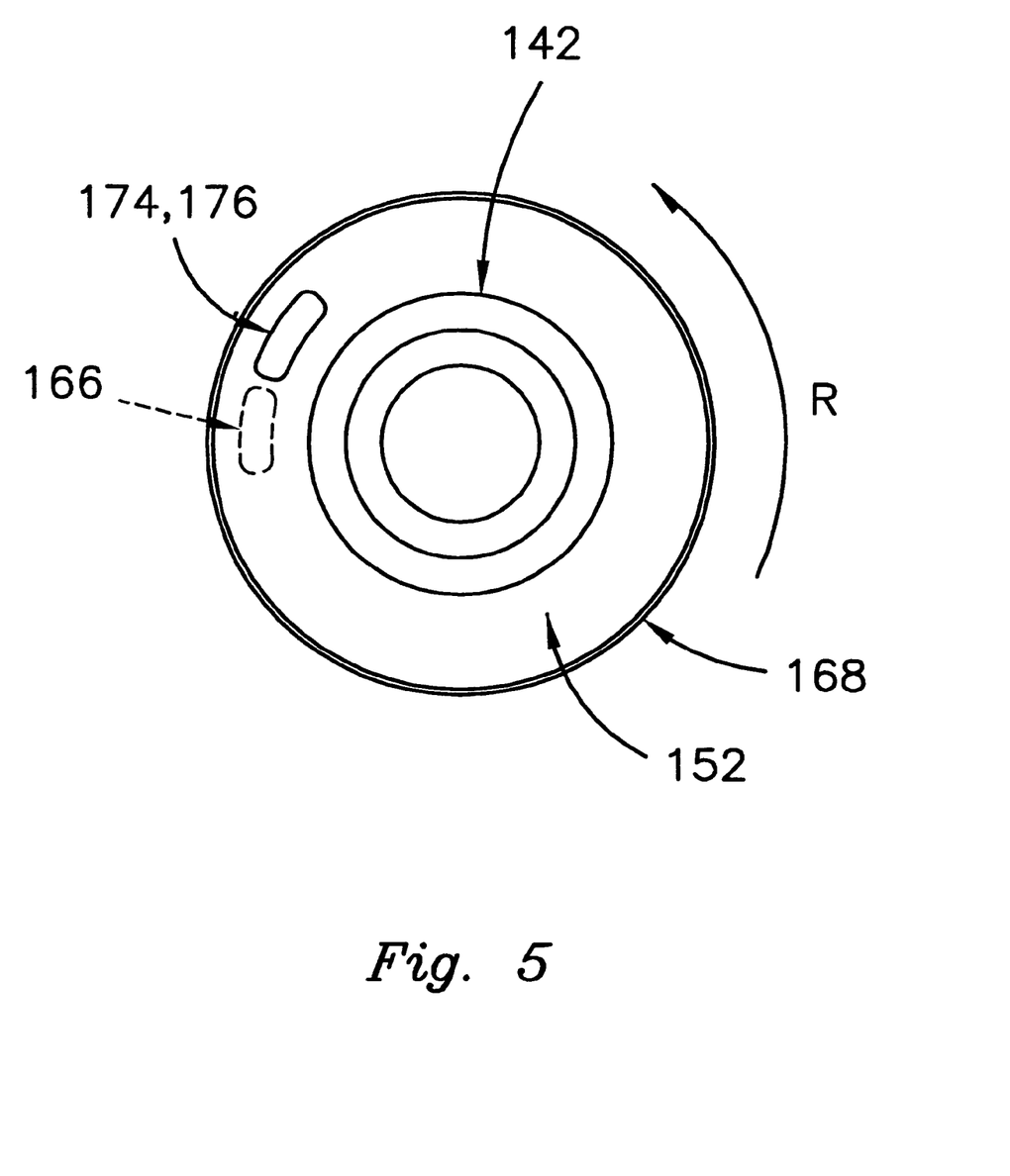
FIG. 5 shows a top view of components of the suction-irrigation probe shown in FIG. 4.

Referring now to FIG. 5, a top view of piston 142 is shown for clarification. As shown in phantom lines superimposed on seal 152 for illustration, a position of slotted passageway 166 formed in shoulder 164 is shown. Also illustrated in FIGS. 4 and 5 is a relative position of slotted passageways 174 and 176 formed in piston 142 and lower seal 152, respectively. Slotted passageways 174 and 176 are most preferably aligned with one another at all times. A spine or notch or rib (not shown) can be provided on piston 142 to prevent relative rotation. As shown in the figure, rotation of piston 142 and seal 152 together in the direction generally designated by the letter "R" can be made to cause alignment of slotted passageways 174 and 176 with slotted passageway 166 in shoulder 164. A keyhole can be provided in the open end of the barrel to accommodate longitudinal ribs on the piston, wherein the keyhole limits the degree of rotation of the piston relative to the barrel. Also, two sets of slotted passageways 174 and 176 are optionally formed in piston 142 and seal 152, separated by 180°, to facilitate proper assembly of the valve.

As shown in FIG. 4, alignment of slotted passageways 166, 174 and 176 together form a flow path between an interior passageway of barb 130 and an interior region of barrel 128. This path can be considered a secondary flow path that is preferably substantially separate from the primary flow path (which extends in the direction from probe body 112, through opening 134, upward through piston bore 144, outward through through-hole 146, and out through barb 130). When the passageways are not aligned to overlap, then seal 152 prevents flow through passageway 166. A raised pad or boss (not shown) can be formed around slotted passageway 166 on shoulder 164 (extending downwardly in the embodiment shown in FIG. 4) in order to encourage a fluid-tight seal between seal 152 and shoulder 166 in a closed position. Accordingly, depression of finger rest 160 and piston 142 with respect to barbed tube 126 in the direction "D" will open a primary flow path, and rotation of finger rest 160 and piston 142 with respect to barbed tube 126 in the direction "R", while piston 142 is in the uppermost position shown in FIG. 4, will open a secondary flow path through the slotted passageways 166, 174 and 176.

Figure 6:
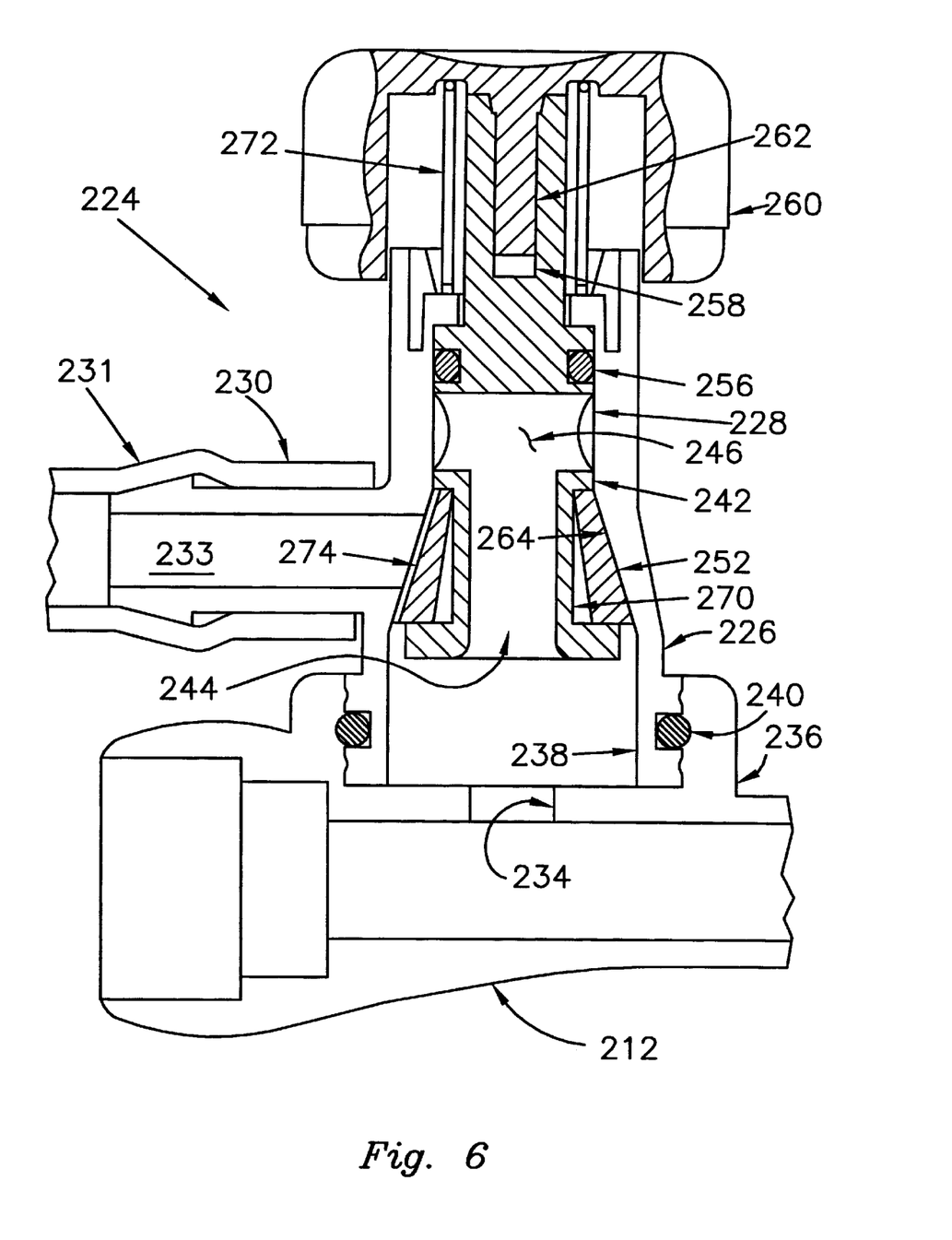
FIG. 6 shows a cross-sectional side view of a portion of yet another embodiment of a suction-irrigation probe according to this invention.

Referring now to FIG. 6, yet another embodiment of a probe according to this invention is generally designated by the numeral "200".

Suction valve 224 includes a barbed tube 226 having a substantially hollow valve barrel 228 and a barb 230 adapted for engaging a flexible hose 231. Barbed tube 226 is connected to a probe body 212 adjacent to a body opening 234 at boss 236. A mounting portion 238 of barrel 228 captures an O-ring 240 to create a fluid-tight seal between probe body 212 and barrel 228. As described with reference to previous embodiments, mounting portion 238 of barrel 228 is adapted to permit rotation of barbed tube 226.

Suction valve 224 also includes a piston 242 that is mounted for reciprocal longitudinal movement within barrel 228. Piston 242 is provided with a piston bore 244 and a transverse circular through-hole 246. Through-hole 246 is optionally modified in the manner of opening 46a (FIGS. 12 and 13). Provided around an outer surface of piston 242 spaced from the bottom edge of piston 242 is a radial recess 270.

A conical seal 252 is provided in the recess 270 formed in piston 242. Conical seal 252 is adapted to form a seal against an angled shoulder 264 formed in barbed tube 226 and barrel 228. This seal extends just above and below a passageway 233 formed in barb 230 when the valve is in the position illustrated in FIG. 6. An O-ring 256 is provided in a groove positioned above through-hole 246. Together, conical seal 252 and O-ring 256 form a seal between an outer surface of piston 242 and an inner surface of barrel 228.

Piston 242 is provided with a shoulder above O-ring 256 for abutment against a stop formed near the top of barbed tube 226 to prevent upward movement of piston 242 beyond the position shown in FIG. 6. A finger rest 260 includes a downwardly extending stud 262 which is engaged within a blind hole 258 formed in the top of piston 242. A compression spring 272 is provided to bias the finger rest 260 toward its upper-most position as shown.

Figure 7:
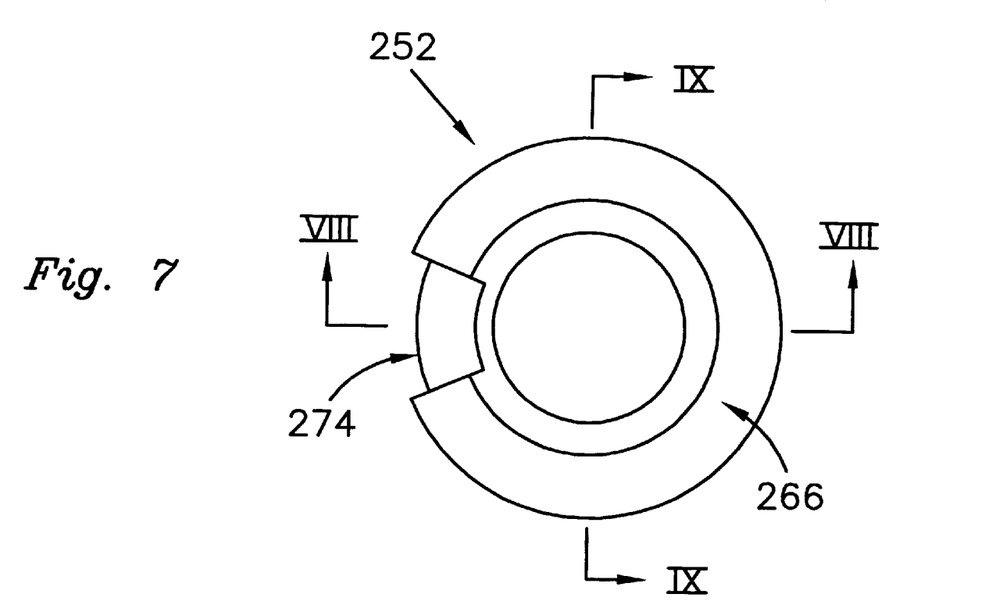
FIG. 7 shows a top view of a component of the suction-irrigation probe shown in FIG. 6.
Figure 8:
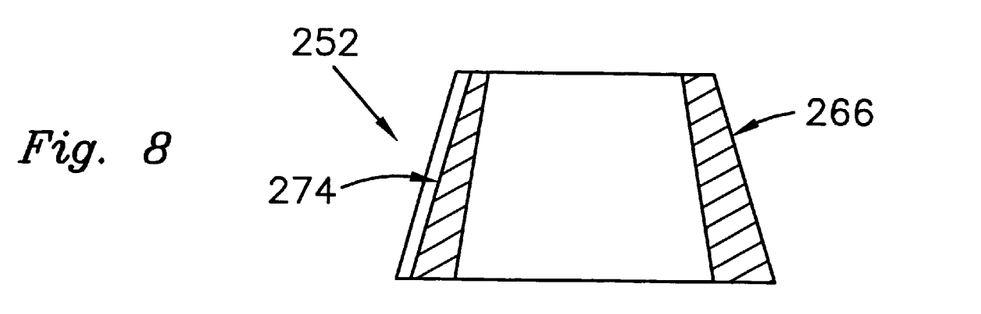
FIG. 8 shows a cross-sectional side view of the component shown in FIG. 7.
Figure 9:
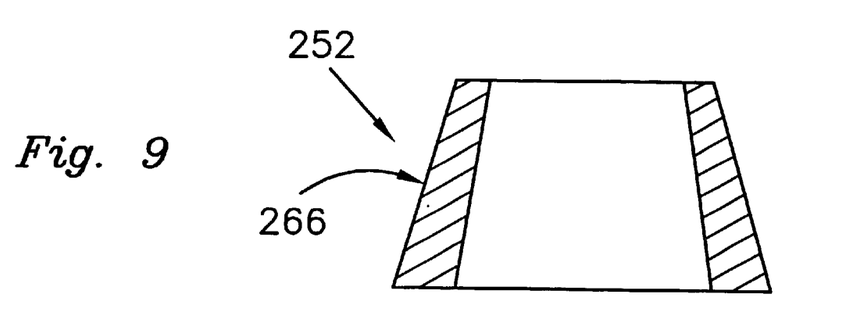
FIG. 9 shows another cross-sectional side view of the component shown in FIG. 7.

Referring now to FIGS. 7–9, preferred details of conical seal 252 are illustrated. The top view shown in FIG. 7 illustrates the position of a flow channel 274 that is formed on an outer sealing surface 266 of seal 252. Although the seal shown in FIG. 7 illustrates a flow channel 274 extending from the bottom surface of seal 252 to the top surface of seal 252, it is contemplated that it need not extend the entire height of seal 252. FIGS. 8 and 9 illustrate cross-sectional side views of seal 252 separated by 90°. Again, flow channel 274 is shown to extend the full height of seal 252 in FIG. 8, but it will be understood that such a flow passage need not extend along the full height. Seal 252 is optionally slit so that it can be installed around piston 242 and bonded to the recessed surface of piston 242. A filler piece (not shown) is optionally added between seal 252 and piston 242, if needed to support the seal. Also, a spine or notch or rib (not shown) can be provided to prevent rotation of seal 252 with respect to piston 242.

Figure 10:
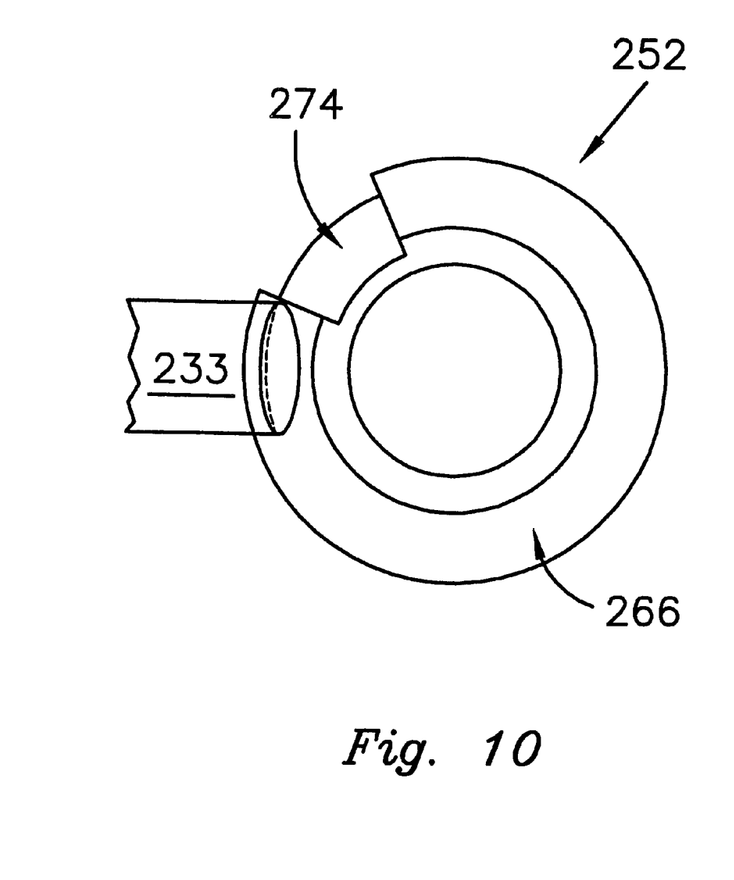
FIG. 10 shows a schematic view of the component shown in FIG. 7, in a substantially closed valve position.
Figure 11:
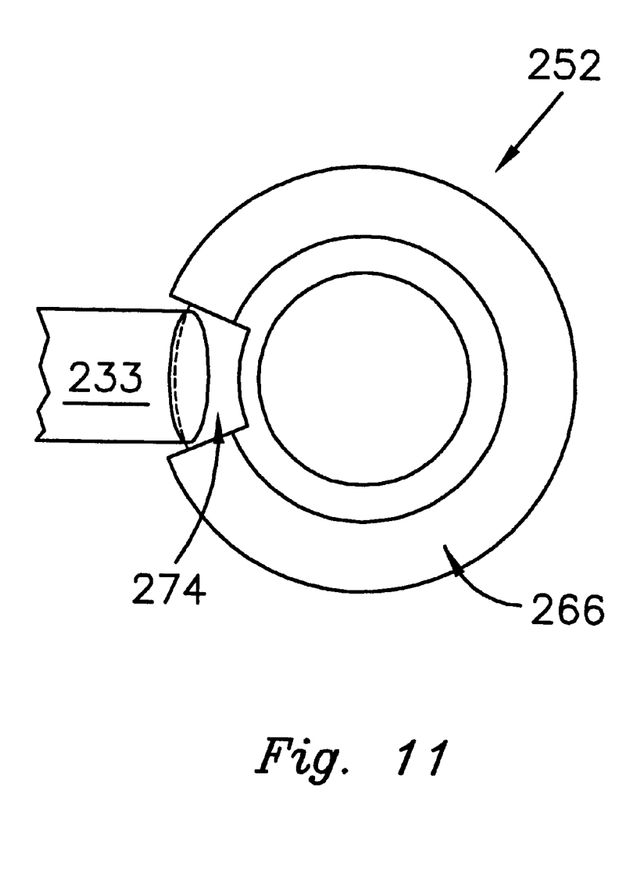
FIG. 11 shows a schematic view of the component shown in FIG. 7 in an open position.

FIGS. 10 and 11 illustrate schematically the significance of flow channel 274 as it relates to passageway 233 when piston 242 is in its uppermost position (FIG. 6). An end opening of passageway 233 is schematically juxtaposed adjacent to seal 252 for purposes of illustration. The orientation of seal 252 with respect to passageway 233 shown in FIG. 10 illustrates a closed position wherein there is no path for flow outward through passageway 233. In contrast, FIG. 11 illustrates full alignment between flow channel 274 and passageway 233, thereby creating a secondary flow path outwardly through channel 274 and passageway 233. The view shown in FIG. 6 illustrates such an open position wherein a secondary flow path is provided from the interior of barrel 228, through flow channel 274, and outwardly through outlet passageway 233. Although FIG. 11 illustrates full alignment between passageway 233 and flow channel 274, partial alignment for partial flow is of course contemplated as with the other embodiments described herein. In other words, the secondary paths can be partially opened to permit a limited flow path, as needed. Partial opening in each illustrated embodiment is accomplished by partial rotation of the piston with respect to the barrel, and means such as ribs and detents can be utilized between the finger rest and barbed tube to define discrete steps of rotation.

The operation of preferred probes 10, 100 and 200 will now be described with reference to the figures. Each probe embodiment is adapted to be held in the hand of a surgeon or other technician, to provide a controlled introduction of fluid into an operative site, and to permit the controlled suction of fluid from the operative site. Depression of finger rests 60, 160, 260 on suction valves 24, 124, 224 permit the flow of liquid or gaseous fluid to a suction source (not shown), through the valves 24, 124, 224 from the probe bodies 12, 112, 212 and from the probe shaft 14. Suction valves 24, 124, 224 are used in a fully opened or fully closed condition when they are alternatively fully depressed or fully released to their rest position, respectively. Also, the finger rests on suction valves 24, 124, 224 are partially or fully depressed in order to cause partial or maximum suction of fluid from an operative site through the probe shaft, through the probe body, and out through the flexible hose to a suction source. Such depression in the direction "D" shown in FIG. 1 opens a primary flow path from the operative site to the suction source. Referring to the embodiments illustrated in the figures, the primary path extends from the operative site, inward through the probe shaft 14, into probe bodies 12, 112, 212, upward through openings 34, 134, 234, through bores 44, 144, 244 and through-holes 46, 146, 246 of pistons 42, 142, 242, and outward through barbs 30, 130, 230 and tubes 31, 131, 231.

In order to perform a partial suction or aspiration of an operative site, such as when smoke is to be evacuated after a cauterization procedure, a smoke evacuation feature as described herein can be utilized to partially and controllably open the suction valve. To do so, finger rests 60, 160, 260 are used to rotate pistons 42, 142, 242 in the direction "R" shown in FIG. 2. Such rotation opens a secondary flow path, which is preferably substantially separate from the primary flow path, for smoke or gas evacuation from the operative site to the vacuum source. For example, a path is formed for flow through probe shaft 14, into probe bodies 12, 112, 212, through openings 34, 134, 234, into barrels 28, 128, 228, and into barbs 30, 130, 230 through a secondary flow path that is opened by rotation of the finger rest. In the embodiment of probe 10 illustrated in FIG. 3, the secondary flow path is formed between an outer surface of piston 42 and an inner surface of barrel 28 as a portion of O-ring 52 fully or partially traverses barb 30 upon rotation of piston 42. In the FIG. 4 embodiment of probe 100, the secondary flow path is formed through slotted passageways 174, 176 and 166 as they become fully or partially aligned with one another upon rotation of piston 142. The FIG. 6 embodiment of probe 200 has a secondary flow path through flow channel 274 as it becomes fully or partially aligned with barb 230 upon rotation of piston 242.

Once rotated, pistons 42, 142 and 242 preferably remain in the smoke evacuation mode until they are readjusted to the closed position. Even while in a rotated position for smoke evacuation, pistons 42, 142 and 242 can be partially or fully depressed to partially or fully open the primary flowpath. This may be desirable when immediate liquid suction is required, for example. Subsequent release of pistons 42, 142 and 242 will return them to their original smoke evacuation setting.

If a preferred probe is provided with a rotatable barrel for adjustment of the position of hoses (as shown in the embodiments in FIGS. 3, 4 and 6), then the torque required for rotating the piston for smoke or gas evacuation is preferably less than the torque required to rotate the suction valve's barrel with respect to the probe body. Accordingly, a surgeon can adjust such a smoke evacuation feature by rotating the finger rest without causing an unintended rotation of the flexible hose about the axis of the suction valve's barrel.

Many modifications to the preferred embodiments shown and described can be made without departing from the spirit and scope of this invention. For example, the probe can be formed in a variety of shapes and sizes and the components of the probe can be provided with a wide variety of configurations and can be formed from a wide variety of materials. Also, although the preferred embodiment includes a valve for suction and a separate valve for irrigation, a probe according to this invention can have a single valve for suction or for irrigation. It is also contemplated that a single valve can be used both for suction and for irrigation depending on the manner in which the probe is connected to the sources of irrigation fluid and suction.

It is also contemplated that the configuration of the valve or valves with respect to the probe's body can be modified significantly depending on design preferences. For example, the barbed tube portion of the valve can also be positioned below the probe body or on the opposite side of the probe body from the finger rest. Referring to FIG. 3 as a point of reference, barbed tube 26 can be positioned below probe body 12 and the top or side of barbed tube 26 can be open to the interior passageway of probe body 12. In such an embodiment, a portion of the barrel can be positioned above the probe body and a portion below, and the bottom of the barrel can be closed. Also, the axis of such a barrel can either intersect with the axis of the passageway of the probe body or not, depending on design preferences. In other words, the axis of the barrel is optionally offset from the axis of the probe body. Again referring to FIG. 3, the barrel can be positioned to the side of probe body 12 so that the barrel axis is offset from the body axis. In such an embodiment, transverse hole 46 is preferably aligned with the side opening of the body in an open valve position.

In any embodiment, a probe according to this invention will have significant benefits. The piston is rotatable with respect to the barrel so that optimal gas or smoke evacuation can be easily accomplished by a surgeon during a surgical procedure. Also, the piston can be separately depressed in the barrel fully or partially for optimal liquid suction, when desired.

While many modifications to the preferred embodiments have been described, it is contemplated that additional modifications can be made without departing from the spirit or scope of the invention, which is defined separately in the claims that follow.

What is claimed is:

1. A valved device adapted for controlling flow into or out from a surgical patient, said valved device comprising:
   a body defining a flow passageway;
   a valve connected to said body in flow communication with said flow passageway, said valve comprising a barrel and a piston extending within said barrel;
   said piston being mounted for selectively displacing said piston longitudinally within said barrel in a direction along the axis of said barrel to selectively permit primary passage flow into or out from said surgical patient; and
   said piston also being mounted for selectively rotating said piston within said barrel in a direction about said axis of said barrel to selectively permit secondary passage flow into or out from said surgical patient;
   said piston being mounted to occupy a longitudinal position in said barrel wherein said means for rotating is adapted to rotate said piston and to selectively permit said secondary passage flow without further axial displacement of said piston,
   and a seal positioned to prevent flow out from said barrel through a port when said piston is in a radial position in which flow in said secondary passage is prevented, and said seal is positioned to permit flow out from said barrel and out said secondary passage when said piston is rotated to a radial position in which said secondary flow is permitted, all without further axial displacement of said piston in said barrel.

2. The valved device defined in claim 1, wherein said means for selectively displacing said piston comprises a member positioned for manual depression of said piston from a closed valve position to an open valve position spaced along said axis of said barrel from said closed valve position.

3. The valved device defined in claim 1, wherein said means for selectively rotating said piston comprises a member positioned for manual rotation of said piston from a closed valve position to an open valve position rotated about said axis of said barrel from said closed valve position.

4. The valved device defined in claim 3, wherein at least a portion of said barrel of said valve is connected to said body for rotation about said axis of said barrel.

5. The valved device defined in claim 4, wherein the torque required for said manual rotation of said piston is less than the torque required to rotate said portion of said barrel.

6. The valved device defined in claim 1, wherein said means for displacing said piston is adapted to open a flow path for flow into or out from a surgical patient and said means for rotating said piston is adapted to open a substantially separate flow path for flow into or out from a surgical patient.

7. The valved device defined in claim 6, wherein said flow path comprises a primary flow path adapted for liquid flow and said substantially separate flow path comprises a secondary flow path adapted for gas flow.

8. The valved device defined in claim 6, wherein said means for displacing said piston is adapted to selectively open said flow path for maximum flow and said means for rotating said piston is adapted to selectively open said substantially separate flow path for restricted flow.

9. A valved device adapted for controlling flow into or out from a surgical patient, said valved device comprising:
   a body defining a flow passageway;
   a valve connected to said body for flow communication with said flow passageway, said valve comprising a barrel and a piston extending into said barrel;
   said piston being mounted for selectively displacing said piston longitudinally within said barrel in a direction along the axis of said barrel to select primary passage flow into or out of said surgical patient; and
   said piston also being mounted to occupy a longitudinal position in said barrel wherein said means for selective rotational movement can be accomplished independent of said axial movement between a radial position with respect to said barrel in which secondary flow is prevented and a rotated radial position with respect to said barrel in which secondary flow is permitted, wherein said secondary flow is selectively permitted or prevented, all without further axial displacement of said piston in said barrel.

10. The valved device defined in claim 9, wherein at least a portion of said barrel of said valve is connected to said body for rotation about said axis of said barrel.

11. The valved device defined in claim 10, wherein the torque required for said rotational movement of said piston is less than the torque required to rotate said portion of said barrel.

12. The valved device defined in claim 9, further comprising a seal positioned to prevent flow out from said barrel through a port when said piston is in said radial position and to permit flow out from said barrel when said piston is in said rotated radial position.

13. The valved device defined in claim 12, wherein said seal is oriented at an angle to a plane perpendicular to said axis of said barrel, and wherein selective rotational movement of said piston causes a portion of said seal to traverse a portion of said port.

14. The valved device defined in claim 12, wherein said seal and said piston together define an opening for flow into said port and a portion of said barrel defines an opening between an interior of said barrel and said port, and wherein selective rotational movement of said piston causes at least partial alignment of said openings.

15. The valved device defined in claim 14, wherein said portion of said barrel comprises a shoulder, and wherein said seal is positioned between a surface of said piston and said shoulder.

16. The valved device defined in claim 12, wherein said seal defines a channel for flow via a secondary flow pathway into said port and is positioned between a portion of said piston and a portion of said barrel, and wherein selective rotational movement of said piston causes at least partial alignment between said port and said channel defined in said seal.

17. The valved device defined in claim 16, wherein said seal comprises a conical sealing surface oriented to sealingly contact a tapered shoulder in said portion of said barrel.

18. A valved device adapted for controlling flow into or out from a surgical patient, said valved device comprising:
   a body defining a flow passageway;
   a valve connected to said body, said valve comprising a barrel mounted to said body for flow communication with said flow passageway defined in said body, a port defined in said barrel for flow into or out from said barrel, and a piston extending into said barrel and mounted for selective longitudinal movement in a direction along an axis of said barrel and for selective rotational movement in a direction about said axis of said barrel;
   means forming a primary flow path through said valve between said flow passageway defined in said body and said port defined in said barrel upon said selective longitudinal movement of said piston along said axis of said barrel; and
   means forming a substantially separate secondary flow path through said valve between said flow passageway and said port upon said selective rotational movement of said piston about said axis of said barrel,
   said piston being mounted to occupy a longitudinal position in said barrel wherein said piston is rotatable to selectively prevent or allow flow through said secondary passage without further axial displacement of said piston in said barrel.

19. The valved device defined in claim 8, wherein said means forming said primary flow path comprises a passageway extending through an interior portion of said piston.

20. The valved device defined in claim 18, wherein said means forming said substantially separate secondary flow path comprises a passageway extending between an exterior portion of said piston and said barrel.

21. A valved device adapted for controlling flow into or out from a surgical patient, said valved device comprising:
   a body defining a flow passageway;
   a valve connected to said body for flow communication with said flow passageway, said valve comprising a barrel and a piston extending into said barrel;
   said piston being mounted for selectively displacing said piston longitudinally within said barrel in a direction along the axis of said barrel to select primary passage flow into or out of said surgical patient; and
   said piston also being mounted for selective rotational movement in a direction about said axis of said barrel between a position with respect to said barrel in which secondary flow is prevented and a rotated 1 position in which said secondary flow is permitted
   wherein said piston is mounted to occupy a longitudinal position in said barrel wherein said piston may be rotated to allow or prevent said secondary flow independently of axial movement of said piston; and
   a seal positioned to prevent flow out from said barrel through a port when said piston is in said radial position and to permit flow out from said barrel when said piston is in said rotated radial position;
   wherein said seal is oriented at an angle to a plane perpendicular to said axis of said barrel, and wherein selective rotational movement of said piston causes a potion of said seal to traverse a portion of said port.

* * * * *